(12) United States Patent
Oostman, Jr. et al.

(10) Patent No.: US 8,465,498 B2
(45) Date of Patent: Jun. 18, 2013

(54) TENSIONING DEVICE AND METHOD FOR HAIR TRANSPLANTATION

(75) Inventors: Clifford A. Oostman, Jr., Hansville, WA (US); James A. Harris, Greewood Village, CO (US)

(73) Assignee: Restoration Robotics, Inc., San Jose, CA (US)

( * ) Notice: Subject to any disclaimer, the term of this patent is extended or adjusted under 35 U.S.C. 154(b) by 242 days.

(21) Appl. No.: 12/688,395

(22) Filed: Jan. 15, 2010

(65) Prior Publication Data

US 2011/0178533 A1 Jul. 21, 2011

(51) Int. Cl.
*A61B 17/50* (2006.01)
(52) U.S. Cl.
USPC .......................................... 606/133; 606/187
(58) Field of Classification Search
USPC .......... 606/133, 187, 215–218, 152; 600/201, 600/213–217, 232, 233, 234, 235
See application file for complete search history.

(56) References Cited

U.S. PATENT DOCUMENTS

| | | | |
|---|---|---|---|
| 1,550,403 A * | 8/1925 | Turkus | 606/1 |
| 4,370,979 A * | 2/1983 | Erickson | 606/1 |
| 4,434,791 A * | 3/1984 | Darnell | 600/233 |
| 4,621,619 A * | 11/1986 | Sharpe | 600/217 |
| 4,896,680 A | 1/1990 | Hirshowitz | |
| 5,089,009 A | 2/1992 | Green | |
| 5,441,540 A | 8/1995 | Kim | |
| 5,449,374 A | 9/1995 | Dunn et al. | |
| 5,486,196 A | 1/1996 | Hirshowitz et al. | |
| 5,531,790 A | 7/1996 | Frechet et al. | |
| 5,662,714 A | 9/1997 | Charvin et al. | |
| 5,759,193 A | 6/1998 | Burbank et al. | |
| 5,769,783 A | 6/1998 | Fowler | |
| 5,785,649 A | 7/1998 | Fowler, Jr. | |
| 5,814,067 A | 9/1998 | Fleischmann | |
| 5,931,777 A | 8/1999 | Sava | |
| 5,964,697 A | 10/1999 | Fowler, Jr. | |
| 5,971,920 A | 10/1999 | Nagel | |

(Continued)

FOREIGN PATENT DOCUMENTS

| | | |
|---|---|---|
| DE | 44 44 130 A1 | 6/1995 |
| WO | 0103588 A1 | 1/2001 |
| WO | 2006132256 A1 | 12/2006 |
| WO | 2008/107110 | 9/2008 |

OTHER PUBLICATIONS

PCT International Search Report in relation to commonly assigned PCT application, PCT/US2010/021353, Applicant: Restoration Robotics, Inc., Forms PCT/ISA/210, 220 and 237, dated Jun. 29, 2010 (20 pages).

(Continued)

*Primary Examiner* — Tuan V Nguyen
*Assistant Examiner* — Tin Nguyen
(74) *Attorney, Agent, or Firm* — Lena I. Vinitskaya; Sharon Upham

(57) ABSTRACT

A device and method for applying tension to an area of skin, in particular for follicular unit removal and/or implantation in a hair transplantation procedure, is provided. The tensioning device comprises at least one body surface grabber capable of engaging the body surface, and the tensioning device is configured to be able to create tension on a body or skin surface by simply displacing the tensioning device as a whole in one general direction. The tensioning device may be secured, for example, to a patient chair.

19 Claims, 2 Drawing Sheets

U.S. PATENT DOCUMENTS

| | | | |
|---|---|---|---|
| 5,972,021 | A | 10/1999 | Huttner et al. |
| 6,036,641 | A | 3/2000 | Taylor et al. |
| 6,120,436 | A | 9/2000 | Anderson et al. |
| 6,159,231 | A | 12/2000 | Looney et al. |
| 6,190,312 | B1 | 2/2001 | Fowler, Jr. |
| 6,254,624 | B1 * | 7/2001 | Oddsen et al. ............... 606/213 |
| 6,464,634 | B1 | 10/2002 | Fraser |
| 6,695,868 | B2 | 2/2004 | Looney et al. |
| 7,208,006 | B2 | 4/2007 | Fleischman |
| 2002/0087051 | A1 | 7/2002 | Levisman |
| 2004/0049206 | A1 | 3/2004 | Rassman |
| 2006/0270909 | A1 | 11/2006 | Davis et al. |
| 2007/0021779 | A1 * | 1/2007 | Garvin et al. ............... 606/216 |
| 2007/0078466 | A1 | 4/2007 | Bodduluri et al. |
| 2007/0282374 | A1 | 12/2007 | Sogard et al. |
| 2008/0027484 | A1 * | 1/2008 | Lee et al. ............... 606/215 |
| 2008/0114395 | A1 * | 5/2008 | Mathisen et al. ............. 606/215 |
| 2010/0030260 | A1 | 2/2010 | Fleischmann |
| 2010/0191253 | A1 | 7/2010 | Oostman et al. |
| 2011/0152627 | A1 * | 6/2011 | Tannoury et al. ............. 600/217 |

OTHER PUBLICATIONS

Invitation to pay Additional Fees Form PCT/ISA/206 and Annex to Form PCT/ISA/206 (communication relating to the results of the Partial international Search) in relation to PCT/US2010/021353, Applicant Restoration Robotics, Inc. dated Apr. 15, 2010 (7 pages).

Non-Final Office Action mailed Jan. 19, 2012, in relation to commonly assigned U.S. Appl. No. 12/688,430 (17 pages).

Office Action dated Jun. 26, 2012, in relation to commonly assigned Australian Patent Application No. 2010206872 (3 pages).

* cited by examiner

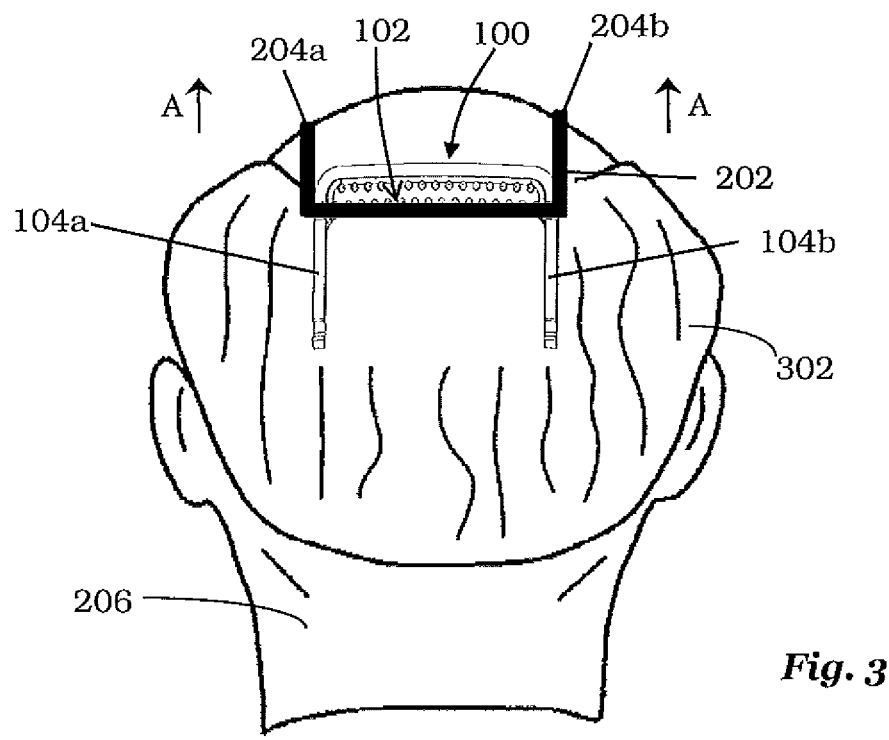
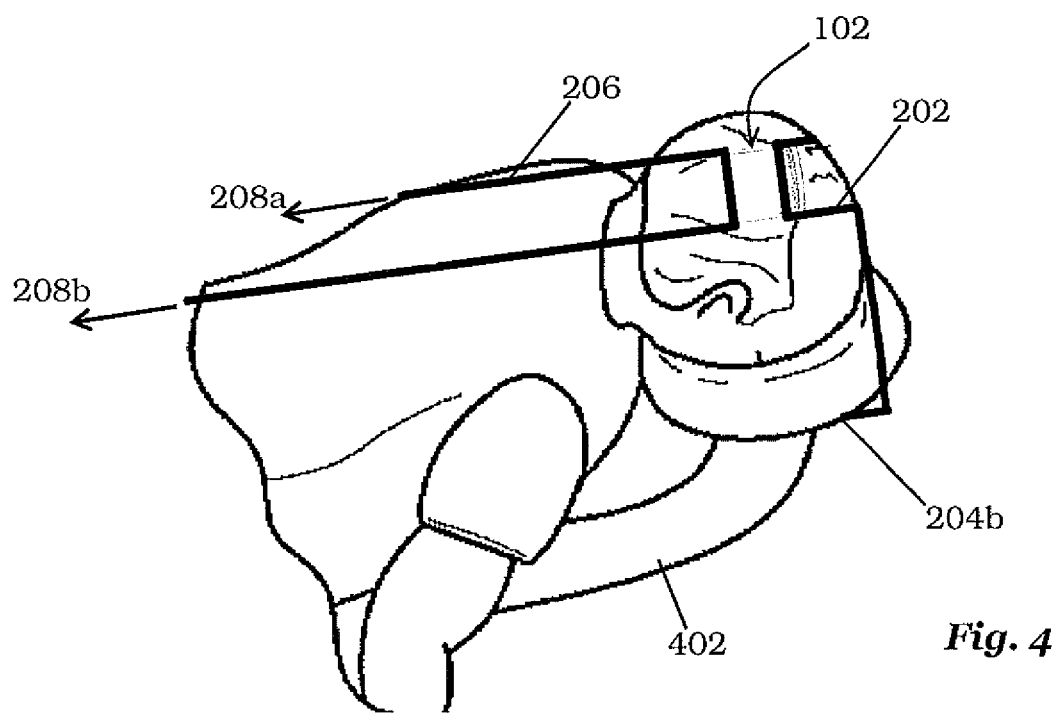
Fig. 3
Fig. 4

TENSIONING DEVICE AND METHOD FOR HAIR TRANSPLANTATION

FIELD OF THE INVENTION

The present invention relates generally to devices, systems and methods for applying tension to an area of a body surface and, in particular, skin tensioners and methods of use in conjunction with hair transplantation procedures.

BACKGROUND OF THE INVENTION

There are numerous surgical, cosmetic, therapeutic and dermatological procedures that involve maneuvering an area of skin. Hair transplantation is one of those procedures and it typically involves harvesting donor hair grafts, e.g. follicular units ("FUs"), from the "donor areas," and implanting them in a bald area ("recipient area"). Hair transplantation is very labor-intensive and complex procedure that requires skill and precision. During hair transplantation procedures, in order to apply tension to a skin surface in the area of hair harvesting or implantation, pressure is typically applied adjacent the target location using two fingers. Similar skin tensioning technique is used in various cosmetic and dermatological procedures other than hair transplantation.

One automated system for harvesting follicular units from a body surface is disclosed in U.S. Patent Publication 2007/0078466. In one embodiment a skin tensioner in the form of two tines presses against a skin surface to thereby tension the skin.

There are also commercially available surgical retractors that hold tissue away from the operating field, including those manufactured by Lone Star Medical Products, Inc. These retractors, however, are not very suitable for skin tensioning required for procedures, such as hair transplantation.

SUMMARY

According to one aspect, a tensioning device is provided for applying tension to a body surface. The tensioning device comprises a frame, at least one body surface grabber configured to engage the body surface, and a displacement mechanism configured to be attached to the frame. When the at least one body surface grabber is engaged with the body surface, the tensioning device is configured to be moved by the displacement mechanism in substantially one direction to cause tension to be created in the body surface. In some embodiments, the displacement mechanism is further configured to be attached at a location somewhere other than on the tensioning device. The displacement mechanism can be removably or permanently attached to the tensioning device, for example, to the frame of the device. A first portion of the displacement mechanism may be attached to the frame of the tensioning device, for example, in a groove formed on the frame. A second portion of the displacement mechanism, which could be an end portion, may be configured to be attachable, for example, to a patient chair, or couch, or similar location. In some embodiments, the tensioning device may comprise a U-shaped frame with two arms and a heel. The at least one body surface grabber may be disposed at the heel of the U-shape frame. In some embodiments, an optional securing member may be provided. The securing member may be configured to be attachable, including removably attachable and detachable, to at least one anchoring location on the tensioning device, which in certain configurations may be the same location as where the displacement mechanism is attached. In other configurations, the anchoring location of the securing member may be spaced apart from the attachment location of the displacement mechanism, In some embodiments, where the frame has two arms, the at least one anchoring location may be disposed on one or both arms of the frame. The anchoring location(s) may be configured to receive and hold the securing member, for example, in a form of a groove, notch, ridge, slot, indent, post, hook, snap or other forms and structures to aid in temporarily or permanently fastening or anchoring the securing member. In some embodiments, the tensioning device may be configured such that a treatment area (such as hair graft harvesting or implantation site) is disposed between the displacement mechanism and the securing member. The at least one body surface grabber may comprise one or more of a barb or a microbarb. The displacement mechanism may comprise a strand, a strap, a belt, or a band. The tensioning device may be configured and sized to tension the body surface which contains hair follicles such that the hair follicles can be harvested from or implanted into the tensioned body surface.

According to another aspect, there is provided a method for tensioning a body surface. The method uses a tensioning device comprising at least one body surface grabber capable of engaging the body surface, and a displacement mechanism capable of being permanently or removable attached to the tensioning device. The method comprises placing the tensioning device on a body surface, engaging the at least one body surface grabber in the body surface, and moving the displacement mechanism such that the tensioning device moves in substantially one general direction to cause tension to be created in the body surface. The method may further comprise removably attaching a portion, for example, an end of the displacement mechanism, to the frame of the tensioning device. When the displacement mechanism comprises a magnetic element, movement of the displacement mechanism may comprise activation of a magnetic field to enable the tensioning device to move in substantially one direction. The method may further comprise using a securing member to prevent flipping or disengaging of at least a portion of the tensioning device from the body surface. The securing member may be a second strand, and using the securing member may comprise attaching the second strand to the frame, for example, to a location spaced away from the location of the attachment of the displacement mechanism or to the same location. The step of engaging the body surface grabber with the body surface may be carried out without compressing the tensioning device. In certain applications, the method can further comprise harvesting hair follicles from the tensioned body surface and/or implanting hair follicles into the tensioned body surface. The method may further comprise disengaging the tensioning device from the body surface, placing the tensioning device at a new location on the body surface and repeating the steps of: engaging the body surface grabber, moving the displacement mechanism to cause tension to be created in the new location on the body surface, and harvesting hair follicles from the new tensioned location on the body surface.

BRIEF DESCRIPTION OF THE DRAWINGS

Features and advantages of the embodiments described herein will become appreciated as the same become better understood with reference to the specification, claims, and appended drawings wherein:

FIG. 3 is a schematic representation illustrating the skin tensioning device of FIG. 2 being used on a patient's head.

FIG. 4 is a schematic representation illustrating a patient seated for treatment on a chair.

DETAILED DESCRIPTION OF THE PREFERRED EMBODIMENTS

Figure 1:
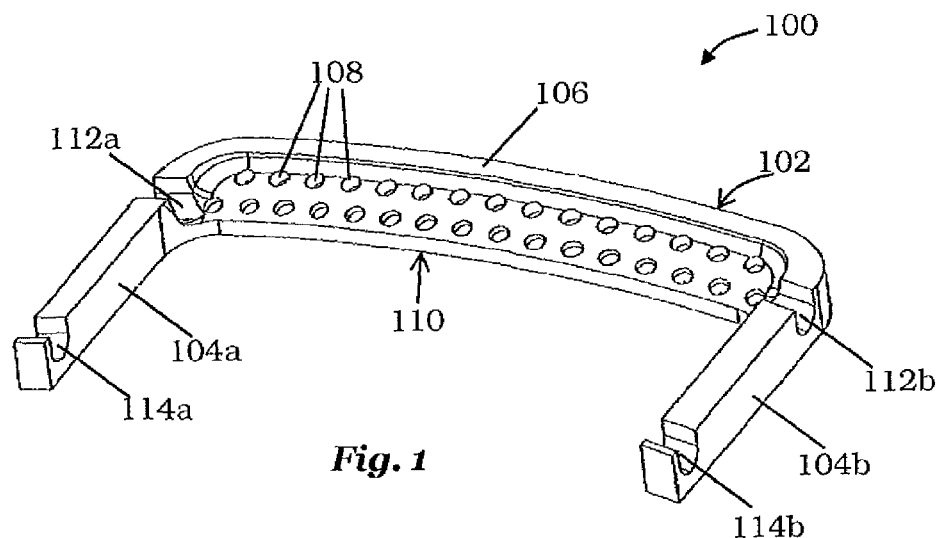
FIG. 1 is a perspective view of an embodiment of a skin tensioning device of the present application, without the securing members being illustrated.

In the following Detailed Description reference is made to the accompanying drawings that show by way of illustration specific embodiments in which the invention may be practiced. In this regard, directional terms, such as "top," "bottom," "front," "back," and "side", etc., are used with reference to the orientation of the Figure(s) being described. Because components or embodiments of the present invention can be positioned in a number of different orientations, the directional terminology is used for purposes of illustration and is in no way limiting. Also, the terms "coupled," or "attached," or "connected," or "mounted" as used herein, means directly or indirectly coupled, attached, connected, integrated, or mounted, for example, through one or more intervening components. It is to be understood that other embodiments may be utilized and structural or logical changes may be made without departing from the scope of the present invention. The following Detailed Description, therefore, is not to be taken in a limiting sense, and the scope of the present invention is defined by the appended claims.

It has been found that commercially available surgical retractors, such as that manufactured by Lone Star Medical Products, Inc. do not provide uniform and consistent skin stretching across the treatment area, for example, in certain cosmetic or dermatological procedures, such as follicle harvesting and/or implantation. Moreover, they are difficult to install, remove, and reinstall if a patient needs to rest. The present application describes a system and method of use for creating tension across a body surface to facilitate various procedures on the body surface, for example, harvesting of follicular units (FUs) from skin or from a scalp. For purposes of clarity, creating tension in a skin surface means applying a tensile force such that the skin surface exhibits lateral tension greater than any tension existing in the relaxed state. Typically, this requires pulling apart, or applying separating forces to, two spaced locations, with the area in between experiencing tension. This is illustrated, for example by the skin tensioning devices described in U.S. Patent Publication 2004/0049206. These tensioning devices require at least two skin contact structures that must be either compressed and/or spread apart in the generally opposing directions in order to create tension. The present application, on the other hand, teaches tensioning devices configured in such a way that they can create tension on a body or skin surface by simply displacing the tensioning device as a whole in one general direction, To apply tensile forces to the body surface, the systems described herein comprise a frame having a contact surface that is or can be configured to lie substantially flush against the body surface. The contact surface comprises some structure, mechanism or features for engaging the body surface. One way to engage the body surface is to provide, for example, barbs extending from the contact surface. In the context of the present application, a "barb" means any small element that projects from the body contact member below the body contacting surface to puncture or form a depression in the body surface. That is, a barb does not necessarily have to be sharp so as to be capable of puncturing the body surface. The term "barb" therefore incorporates needles, pins, points, hooks, nubs, projections, and other similar terms. Furthermore, in certain embodiments and applications of the invention, it is beneficial to use the term "microbarbs." The term "microbarb" refers to a small barb having a maximum size characteristic, typically its diameter (or cross-sectional dimension regardless of the shape; reference in this context to the diameter does not mean that the cross-section is necessarily circular). For example, in one embodiment the microbarb comprises a barb that has a diameter of about 0.127-0.305 mm (0.005-0.012 inches). Also, the microbarb may be defined relative to the barb in terms of surface density, for example, the size of the microbarbs allows them to be placed within 1-5 mm from each other and to more uniformly cover the surface area. Larger barbs, on the other hand, require greater spacing and thus present a less dense array.

Although barbs are described herein as a primary example of ensuring good grip to the skin, other solutions that merely increase the coefficient of friction are contemplated as well. For instance, a frame with a contact surface having adhesive may be successfully utilized in conjunction with certain embodiments described herein. Another possibility is mating Velcro patches, with one temporarily adhered to the skin and one to at least a portion of an underside or bottom surface of the frame. Alternatively, suction could be utilized in certain embodiments. As such, the term "body surface grabber" as used herein encompasses various structures and ways of engaging the skin or body surface, such as by increasing the lateral resistance to movement of the frame across the skin surface in contrast to a smooth-bottomed surface. That is, "body surface grabber or grabbers" encompass barbs, microbarbs, suction, adhesives, Velcro, ribs, ridges, pins, etc., and even rough surface texture.

According to an aspect of the present application, a body surface tensioning device is provided that allows the user to provide substantially uniform tension in a body surface across the relevant treatment area. FIG. 1 illustrates a perspective view of one example of a body surface tensioning device 100 having a U-shaped frame 102. The frame 102 may comprise two arms 104a and 104b and a heel 106. Various fiducials visible under image guidance may be attached to the frame 102, thus providing a convenient reference framework for aiming follicular unit removal or implant tools. The frame 102, or at least a portion of it, such as the heel 106 may have a plurality of perforations 108 for receiving one or more body surface grabbers (not shown) as described above. The perforations 108 although illustrated as extending from the top and through to the bottom surface of the frame 102, may take other forms, such as recesses or openings in the underside or bottom surface 110 (e.g. contact surface 110), that do not extend through to the top surface of the frame. Alternatively, no perforations 108 may be present, and the body surface grabber(s) may be, for example, located or formed on, or otherwise connected to the underside (or bottom) surface 110. The barbs extend beyond (below) the underside or the bottom surface 110 and provide an anchor on a body surface. In the configuration illustrated, there are two rows of perforations 108, but the number of perforations and/or their configuration is not limited in this regard. It will be apparent to the reader that any number or configuration of perforations, or number of rows that enable the device to function appropriately, may be employed. The barbs and microbarbs may be arranged in multiple rows, or they may be staggered to achieve higher density. Also, some of the barbs may have different depth compared to the other barbs, for example, the depth of barbs may range approximately between 1 and 4 mm. For example, one row of barbs may have the same depth of 1 mm while the other row of barbs may have a depth of 2 or more mm. A plurality of the body surface grabbers, for example barbs or hooks, may extend beyond the lower surface 110 of the heel 106 of the tensioning device 100 illustrated in FIG. 1, projecting therefrom. The lower surface or contact surface 110 may be curved or formed such that when in use, the frame conforms to and/or rests closer to the body surface in question. The curvature may be symmetrical or asymmetrical across the surface 110, and may be appropriately shaped to fit the body surface in question. In one particular configuration, for example when used to assist in hair harvesting from a donor area on the scalp, the surface 110 may comprise a spherical radius to approximate to the shape of the scalp. The body surface grabbers may protrude for example from the lower surface 110 of the body surface tensioning device in the range of 1.5 to 2.5 mm, for example. This length of protrusion typically being sufficient to grab or engage the body surface for tensioning purposes. The body surface grabbers provide an anchor for the frame 102 on the body surface BS.

Figure 2:
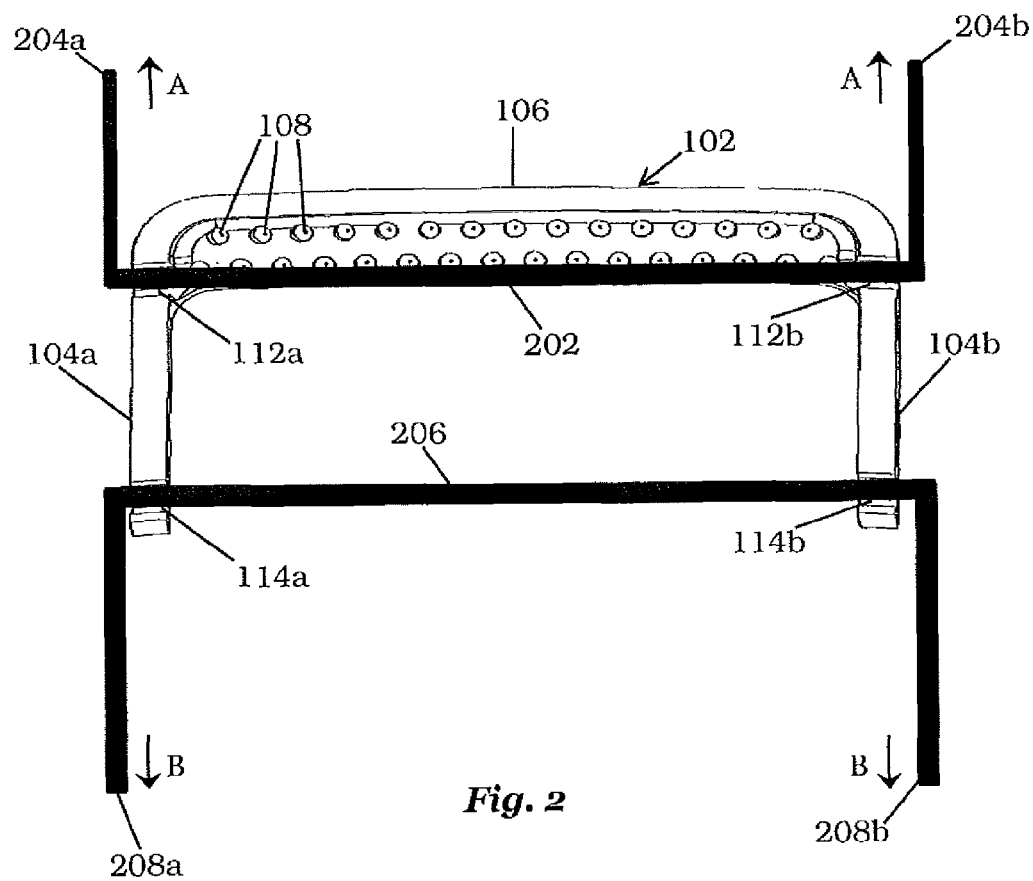
FIG. 2 is a top view of the skin tensioning device of FIG. 1, illustrating how the securing members may be attached thereto.

FIG. 2 shows a top view of the tensioning device 100 of FIG. 1, incorporating an example of a displacement mechanism 202, which in this embodiment takes the form of a strand, strap, belt, or a band (generally referred to herein as a "strand"). The frame 102 comprises two locations 112a and 112b (shown more clearly in FIG. 1) in the form of grooves, which are configured to accommodate and/or anchor the displacement mechanism 202. In some embodiments, instead of grooves, other forms and structures to aid in temporarily or permanently fastening or anchoring the displacement mechanism could be used, for example, notches, ridges, slots or holes, indents, posts, hooks, or snap-type connections. The displacement mechanism 202 is configured to be attached permanently, or removably, to the frame 102. In this particular configuration, the displacement mechanism 202 extends across the frame 102 from one arm 104a to the other arm 104b, which enables a substantially uniform tension to be attained when the tensioning device is in use. The free ends 204a and 204b of the displacement mechanism are configured to be fixed, or tied, or otherwise connected (including removably connected) to a location somewhere other than on the tensioning device, for example, a chair or a couch on which the patient is placed during treatment. The chair may provide a place where the free ends 204a and 204b can be securely anchored.

FIG. 3 shows the tensioning device 100 employed on the back of the head 302 of a patient. In this embodiment, the displacement mechanism 202 extends across the frame 102, and the free ends 204a and 204b of the displacement mechanism extend in a direction A as they proceed up and over the patient's head 302. When the body surface grabbers are engaged in the body surface, operation of the displacement mechanism 202 causes the tensioning device 100 to move in substantially one general direction, direction A. As a consequence of this movement, tension is created in the body surface.

In the case of the body surface being the scalp of a patient's head 302 as illustrated, once the body surface grabbers have engaged the scalp and the displacement mechanism 202 has been attached, for example, via grooves 112a and 112b, operation of the displacement mechanism 202 may be achieved by manually pulling the ends 204a and 204b of the displacement mechanism 202 in the general direction A. Pulling the displacement mechanism 202 in this general direction causes the tensioning device 100 to move substantially in one general direction, direction A, which in turn causes the patient's scalp to move towards the front of the patient's head 302. At least a portion of the slack in the patient's scalp that existed prior to the free ends 204a and 204b of the displacement mechanism 202 being pulled is taken up, and tension is therefore created in the body surface. The user may continue to pull the displacement mechanism 202 until a desired tension is established across the body surface, at which point the user can attach the free ends 204a and 204b to a fixed anchoring location such as, for example, the chair 402 on which the patient is placed during treatment. Treatment, for example, hair harvesting and/or implanting of hair follicles may then be performed. Having provided treatment to the tensioned body surface, the tensioning device can be disengaged from the body surface, and placed at a new location on the body surface. The body surface grabbers can then be engaged in the body surface at this new location and tension be created at this new location as described hereinbefore. Treatment, for example, hair harvesting and/or implanting may then be performed at this new location. It will be apparent that these steps may be repeated for as few or as many times required to complete treatment over the desired area.

The frame 102 has a minimum predetermined width associated with it, for example to achieve necessary contact surface and/or accommodate body surface grippers. In some embodiments, the frame, or at least a portion of it, may have an urge to lift across its width, as the tensioning device 100 moves substantially in the one general direction A. This problem is further magnified in the embodiment illustrated, because the structure also comprises the two arms 104a and 104b of the U-shape frame. As a consequence, the two arms 104a and 104b of the U-shape frame may be urged to flip upwards toward the user, away from the patient's scalp. At least a portion of the tensioning device may therefore be caused to disengage from the body surface. To alleviate or at least minimize this problem, it may be advantageous to provide a securing member 206 which stabilizes the frame 102 of the tensioning device 100 and allows it to remain seated on the body surface, for example, on the illustrated patient's head, despite movement in general direction A. The frame 102 may further comprise two anchoring locations 114a and 114b, shown as an example in FIGS. 1 and 2 in the form of grooves on the arms 104a and 104b, which are configured to accommodate a securing member 206. In this particular configuration, the securing member 206 may be also a strand (a belt, a band, or a strap) that like the displacement mechanism 202 extends across the frame 102 from one arm 104a to the other 104b. The ends 208a and 208b of the securing member 206 extend and are configured to be fixed, connected, or anchored to a location somewhere other than on the tensioning device, for example, a chair 402, shown in FIG. 4. The location/chair provides a place where the ends 208a and 208h can be securely anchored. This securing member 206 may be utilized to provide alterative or additional functions. For example, the securing member 206 could also provide supplemental tensioning, though it is not required that it do so. Alternatively it may be used to retain gauze or other such materials to capture blood and/or saline that may drip during the treatment or procedure.

There are numerous ways in which the displacement mechanism and/or the securing member can be configured. For example, the displacement mechanism and/or the securing member may be flexible and/or elastic and fixed to the anchoring location on the frame prior to pulling the ends sufficiently to secure them to the desired locations, such as on the patient's chair 402. Alternatively, the displacement mechanism and/or the securing member may be flexible and/or elastic and fixed to the desired locations, such as on the patient's chair 402 prior to pulling the free ends sufficiently to secure them to the anchoring locations on the frame. In yet another alternative configuration, the frame 102 may comprise a plurality of through bore for receiving and anchoring a plurality of strands, which can be also anchored at locations other than on the tensioning device. In yet another configuration, the displacement mechanism and/or the securing member may comprise an inelastic strand of fixed length, with tension variation of the strand being provided by a tensioning mechanism such as a knob around which the inelastic strand can be wrapped to provide the tension variation. In a further alternative, the securing member may be inflexible and/or not stretchable. Instead, a selection of multiple alternative anchorage locations may be provided on the chair and/or on the frame of the tensioning device, thus providing an alternative means to achieve the desired tensioning.

In yet a further alternative configuration, the displacement mechanism and/or the securing member comprises a strand which forms a closed loop configuration (that is, with no free ends). One end of the loop being attached to the anchoring location on the frame, the other end of the loop being attached to the other anchoring location that resides somewhere other than on the frame. This configuration may further comprise a tension variation device attached to the displacement mechanism and/or the securing member, providing a means to apply a varied tension to the body tensioning device. The tension variation device may incorporate an inner spool or friction wheel (not shown) for pulling on the associated displacement mechanism and/or the securing member. For example, the displacement mechanism and/or the securing member may wrap around a spool rotated by the knob. This provides the user with greater control of the amount of tension in the displacement mechanism and/or the securing member.

It will be appreciated that there are other displacement mechanism and/or the securing member configurations that would adequately serve the purpose which are not limited to having strands as an element thereof. It will also be appreciated that the displacement and/or the securing member configurations are not limited to structures that require a flexible or elastic member to be stretched, or pulled. Instead, the displacement and/or the securing member(s) may be configured, for example, to be non-flexible, and it could be pushed instead of pulled, and still serve the same purpose. The displacement and/or securing member may also comprise, for example, a solid but flexible projection from the tensioning device that can be secured by placing it into a slot with a locking mechanism, such as a thumbscrew, somewhere outside of the tensioning device, for example, on a patient chair. Alternately, the displacement and/or securing member may comprise a slot at a location on the frame, and a solid but flexible projection can be secured to the frame of the device by placing it into the slot. A series of one-way ratchet teeth all inclined in a common direction from one of the ends of the projection may facilitate locking, if the projection is pulled or pushed one way, and enable easy release when encouraged in the opposite direction.

In another example, rather than being in the form of a flexible or elastic member, a configuration that relies upon magnetism, for example, could be utilized. A strip of metal or magnetic material could be disposed on the top surface of the frame, and a magnetic field source could be provided at a location somewhere other than the frame of the tensioning device. The magnet field source could then be activated to provide sufficient magnetic field strength to cause the magnetic material to be attracted in the direction of the magnetic field, and cause the tensioning device to move. The magnetic arrangement may be a semi-permanent one, or permanent. Another example of a displacement mechanism and/or the securing member is one that utilizes air cylinders or springs. For example, two or more non-flexible strands may be connected by air cylinders or springs. The air cylinders or springs may be configured, when activated, to cause the strands to be either pulled together or pushed apart.

In yet another example, where the tensioning device is used in a robotic procedure (such as robotic hair transplantation procedure), the displacement mechanism may be configured in the form of a mechanical protrusion or a member/arm that may be positioned, connected or attached to a robotic system. In this example, robotic activation of the mechanical protrusion/arm/member may cause at least a portion of the protrusion/arm/member to be moved and/or positioned at some location on the frame of the tensional device and to apply a force in a controlled manner and direction to tension the body surface to the desired tension.

According to another aspect of the application, the tensioning device may indicate the amount of tension provided in displacement mechanism and/or the securing member. For example, in the embodiment of the tension adjuster having a spool, the knob may have markings such that the number of rotations may be monitored with the level of tension being relative to the extent of rotation. Calibrated markings may also be provided.

Of course, there are numerous other ways to indicate tension in the displacement mechanism and/or the securing members, such as more complicated and typically more expensive analog or digital numerical force displays. The present application contemplates any number of indicators from the most simple to the most involved. Tension indicators help the user establish the proper body surface tension. A minimum level of tension is desired, in particular for hair follicle removal to tension the skin surface. Furthermore, a predetermined minimum level of tension helps a removal tool such as a needle pierce the skin without cutting excessive flaps of skin around the follicular unit. However, the tension should be limited to a maximum to avoid excessive trauma to the skin surface. Finally, indicators of tension in each securing member enable the user to balance the amount of tension to avoid applying too much to one location or another.

Although the figures and associated text have incorporated a U-shaped configuration of the frame, it will be apparent that different shapes of frames, including a frame with a single heel 106 without the arms 104*a* and 104*b* could be utilized to accomplish tensioning. In this configuration, there is be no need for the additional securing member, providing for a more simplistic and inexpensive device. It will be apparent that other shaped configurations could be suitably employed.

The frame 102 may include fluid flow channels therein. Saline or other inert fluid may be supplying through a port in the frame 102 and distributed to the treatment area within the frame 102, or from around the periphery of the treatment area. The fluid irrigation will mix with any blood or other fluids in the treatment area, and aspirating ports in the side sections of the frame may provide suction to remove excess fluid.

It will be appreciated that tensioning according to the present application can be provided without first compressing at least two spaced apart structures. The tensioning devices and methods described herein do not require the user to apply compressional forces, either manually or using some kind of a tool, to engage the body surface grabbers in the body surface or to create tension in the body surface. Rather the tension is created by displacing the tensioning device as a whole in one general direction. The combination of the displacement mechanism and the body surface grabber provides a simple, inexpensive and possibly disposable solution to the body tensioning problem.

While the preferred embodiments were described, it is to be understood that the words which have been used are words of description and not of limitation, and those skilled in the art will recognize that various modifications and improvements may be made to the invention without departing from the scope thereof. Moreover, although individual features of one embodiment may be discussed herein or shown in the drawings of the one embodiment and not in other embodiments, it should be apparent that individual features of one embodiment may be combined with one or more features of another embodiment or features from a plurality of embodiments.

What is claimed is:

1. A tensioning device for applying tension to a skin surface during a medical procedure, comprising:
   a displacement mechanism;
   a securing member;
   a frame comprising at least one anchoring location for receiving the displacement mechanism, a heel and two arms, wherein the heel and each of the two arms having a skin contact surface;
   at least one of the skin contact surfaces comprising at least one body surface grabber, wherein the at least one body surface grabber is configured to engage the skin surface; and
   the frame further comprising an anchoring location for receiving the securing member, wherein the securing member is configured to secure the frame to the skin surface;
   wherein, the frame is configured to be moved by the displacement mechanism in substantially one direction along the skin surface such that to cause tension in a treatment area on the skin surface while the medical procedure is being performed.

2. The device of claim 1, wherein the displacement mechanism comprises a first portion configured to be attached to the at least one anchoring location and a second portion configured to be attached at a location somewhere other than on the tensioning device.

3. The device of claim 1, wherein the displacement mechanism is removably or permanently attached to the frame of the tensioning device.

4. The device of claim 2, wherein a first portion of the displacement mechanism is attached to the frame of the tensioning device and a second portion of the displacement mechanism is attached to a patient chair.

5. The device of claim 1, wherein the at least one body surface grabber is disposed on the skin contact surface of the heel.

6. The device of claim 1, wherein the securing member is configured to retain a material to capture fluids from the procedure.

7. The device of the claim 1, wherein the securing member is configured to provide supplemental tension.

8. The device of claim 1, wherein the treatment area is disposed between the displacement mechanism and the securing member.

9. The device of claim 1, wherein the at least one body surface grabber comprises one or more of a barb or a microbarb.

10. The device of claim 1, wherein the displacement mechanism comprises a strand.

11. The device of claim 1, wherein the device is configured and sized to tension the body surface containing hair follicles such that the hair follicles can be harvested from or implanted into the tensioned skin surface.

12. The device of claim 1, wherein the at least one body surface grabber comprises adhesive or suction.

13. The device of claim 1, wherein each of the anchoring locations comprises a groove.

14. The device of claim 1, wherein the displacement mechanism comprises a magnetic element such that movement of the tensioning device is enabled by activation of a magnetic field.

15. The device of claim 1, wherein the displacement mechanism comprises an inelastic strand of substantially fixed length, and the frame further comprising a tensioning mechanism configured to provide variable tension.

16. The device of claim 1, wherein the displacement mechanism has a closed loop configuration.

17. The device of claim 1, further comprising a tension indicator to indicate the amount of skin tension.

18. The device of claim 1, wherein the frame is configured to conform to the skin surface.

19. The device of claim 1, the frame further comprises a fluid flow channel configured to provide fluid to a treatment area.

* * * * *